United States Patent
Zenker et al.

(10) Patent No.: US 10,687,854 B2
(45) Date of Patent: Jun. 23, 2020

(54) ACROMIOCLAVICULAR HOOK PLATE

(71) Applicant: DePuy Synthes Products, Inc., Raynham, MA (US)

(72) Inventors: Martin Zenker, Zuchwil (CH); André Galm, Basel (CH); Daniel Andermatt, Möhlin (CH); Martin Bammerlin, Basel (CH); Gianluca Tordi, Riccione (IT); Martin Jaeger, Freiburg (DE)

(73) Assignee: DePuy Synthes Products, Inc., Raynham, MA (US)

( * ) Notice: Subject to any disclaimer, the term of this patent is extended or adjusted under 35 U.S.C. 154(b) by 306 days.

(21) Appl. No.: 15/608,876

(22) Filed: May 30, 2017

(65) Prior Publication Data
US 2018/0344356 A1 Dec. 6, 2018

(51) Int. Cl.
| A61B 17/56 | (2006.01) |
| A61B 17/58 | (2006.01) |
| A61B 17/80 | (2006.01) |
| A61F 2/30 | (2006.01) |
| A61B 17/68 | (2006.01) |

(52) U.S. Cl.
CPC ......... *A61B 17/683* (2013.01); *A61B 17/808* (2013.01); *A61B 17/809* (2013.01); *A61B 17/8061* (2013.01); *A61B 17/80* (2013.01); *A61B 2017/564* (2013.01); *A61F 2/30* (2013.01)

(58) Field of Classification Search
CPC combination set(s) only.
See application file for complete search history.

(56) References Cited

U.S. PATENT DOCUMENTS

| 8,523,919 B2 | 9/2013 | Huebner |
| 2007/0185493 A1* | 8/2007 | Feibel ............... A61B 17/8061 606/71 |
| 2007/0233112 A1 | 10/2007 | Orbay et al. |
| 2015/0282850 A1 | 10/2015 | Fierlbeck et al. |
| 2015/0366570 A1 | 12/2015 | Mebarak |

FOREIGN PATENT DOCUMENTS

| CN | 103 750 894 | 4/2014 |
| EP | 1 743 586 | 1/2007 |

* cited by examiner

*Primary Examiner* — Sameh R Boles
(74) *Attorney, Agent, or Firm* — Fay Kaplun & Marcin, LLP

(57) ABSTRACT

A bone plate for treating acromioclavicular dislocations includes a shaft including a lateral portion sized and shaped to be positioned along a superior aspect of a lateral clavicle, the shaft including a plurality of openings extending therethrough for receiving bone fixation elements therein and a hook member extending from the shaft so that, in an operative position, the hook member is hooked under an acromion and the lateral portion of the shaft is positioned on the superior aspect of the lateral clavicle, the lateral portion of the shaft being substantially rounded so that the hook member is movable in one of an anterior direction and a posterior direction while the shaft maintains contact with the superior aspect of the lateral clavicle without any portion of the lateral portion of the shaft protruding beyond a surface of the lateral clavicle.

15 Claims, 7 Drawing Sheets

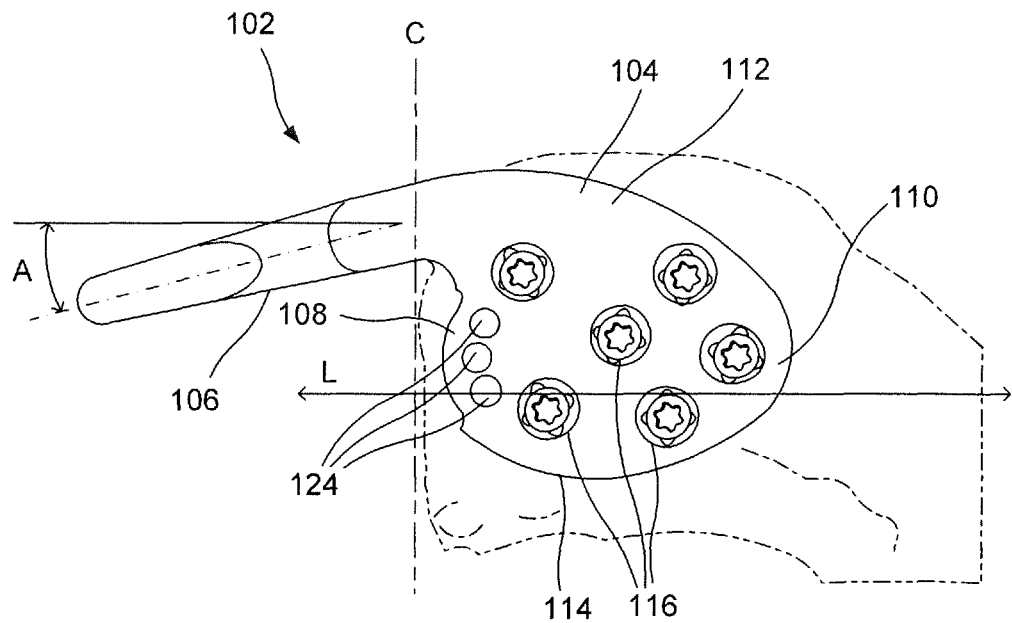
F I G. 7
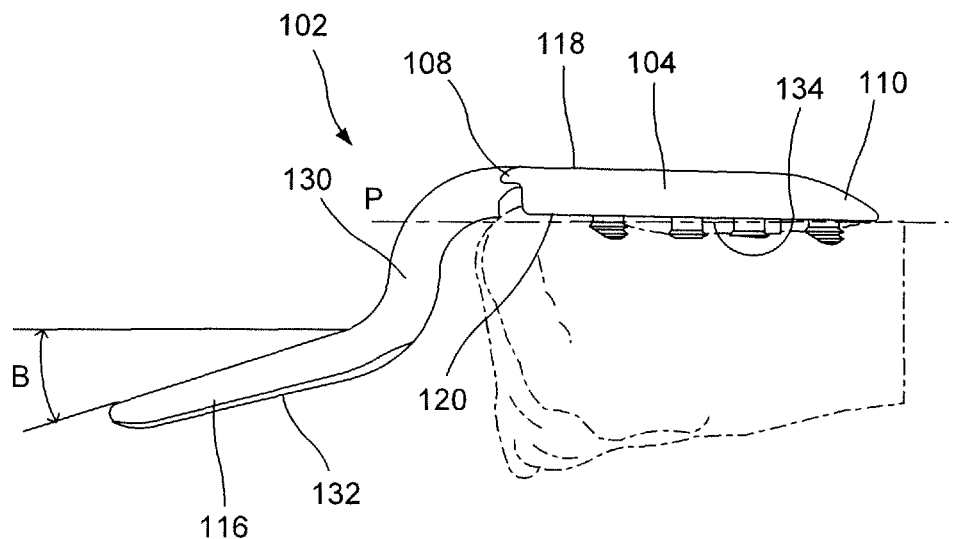
F I G. 8

ACROMIOCLAVICULAR HOOK PLATE

BACKGROUND

Acromioclavicular (AC) joint dislocations caused by ruptures of the AC and coracoclavicular (CC) ligaments are commonly treated with osteosynthesis plates, which include a hook member for hooking under the acromion and a shaft portion for positioning along a lateral portion of the clavicle. These osteosynthesis plates, however, are generally not specifically designed for treating AC joint dislocations. Rather, osteosynthesis plates are generally designed to treat isolated lateral clavicle fractures, lateral clavicle fractures in combination with AC and CC ligament injuries and isolated AC joint dislocations. Thus, in some cases, it may be difficult to optimally place the hook member of an osteosynthesis plate under the acromion while, at the same time, positioning the shaft portion of the osteosynthesis plate on the lateral clavicle. In addition, in some case, the osteosynthesis plate may not be suited to a patient's specific anatomy, leading to conditions such as subacromial impingement and osteolysis, which creates pain and potentially leads to fractures of the acromion or early removal of the plate.

SUMMARY

The present disclosure relates to a bone plate for treating acromioclavicular dislocations, comprising a shaft including a lateral portion sized and shaped to be positioned along a superior aspect of a lateral clavicle, the shaft including a plurality of openings extending therethrough for receiving bone fixation elements therein and a hook member extending from the shaft so that, in an operative position, the hook member is hooked under an acromion and the lateral portion of the shaft is positioned on the superior aspect of the lateral clavicle, the lateral portion of the shaft being substantially rounded so that the hook member is movable in one of an anterior direction and a posterior direction while the shaft maintains contact with the superior aspect of the clavicle without any portion of the lateral portion of the shaft protruding beyond a surface of the lateral clavicle.

The present disclosure also relates to a system for treating an acromioclavicular dislocation, comprising a bone plate including a shaft and a hook member extending therefrom so that, in an operative position, the hook member is hooked under an acromion and a lateral portion of the shaft is positioned on the superior aspect of the lateral clavicle, the lateral portion of the shaft being sized and shaped so that the hook member is movable in one of an anterior direction and a posterior direction while the lateral portion of the shaft maintains contact with the superior aspect of the clavicle without any portion of the shaft protruding beyond a surface of the lateral clavicle and a reduction device including a base portion configured to be releasably coupled to the shaft of the bone plate and a handle member extending from the base portion at an angle.

The present disclosure also relates to a method for treating an acromioclavicular dislocation, comprising hooking a hook member of a bone plate under an acromion, reducing a clavicle by pushing the clavicle with a shaft of the bone plate until a lateral portion of the shaft is positioned along a superior aspect of the lateral clavicle, rotating the bone plate to direct the hook member in one of an anterior direction and a posterior direction to optimize contact between the acromion and the hook member, wherein during a rotation of the bone plate the lateral portion of the shaft maintains contact with the superior aspect of the lateral clavicle with no portion of the lateral portion protruding from a surface of the lateral clavicle, and maintaining a relative position between the acromion and the clavicle and fixing the bone plate to the clavicle by inserting bone fixation elements through openings extending through the shaft.

BRIEF DESCRIPTION

FIG. 7 shows a top plan view of the plate of FIG. 1;

FIG. 8 shows a side (anterior-posterior) view of the plate of FIG. 1;

DETAILED DESCRIPTION

Figure 1:
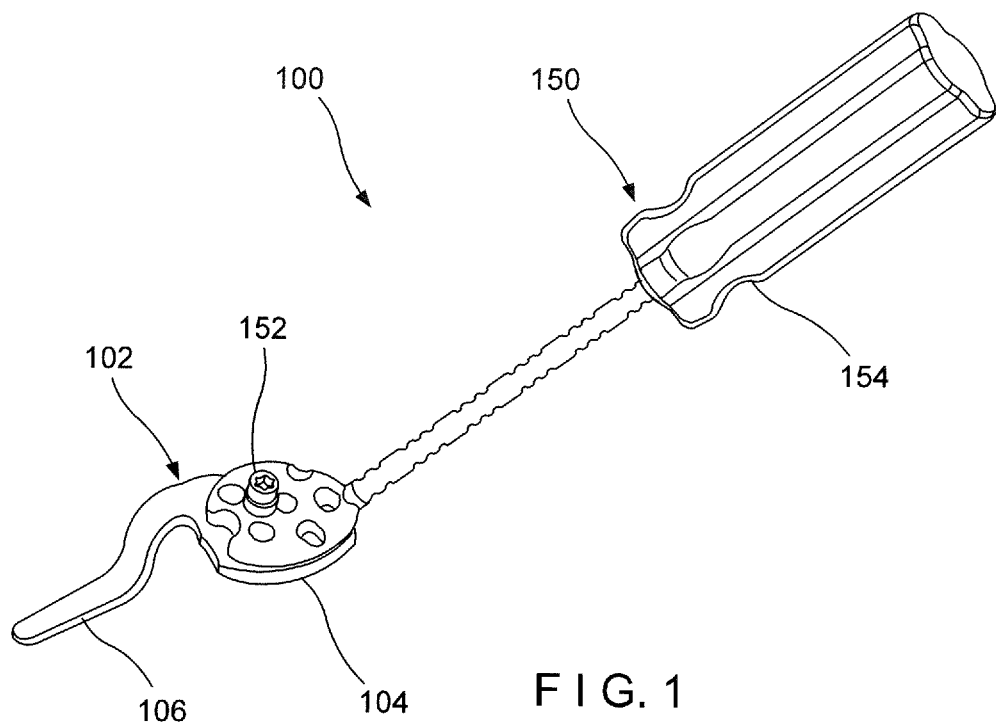
FIG. 1 shows a system according to an exemplary embodiment of the present disclosure.
Figure 2:
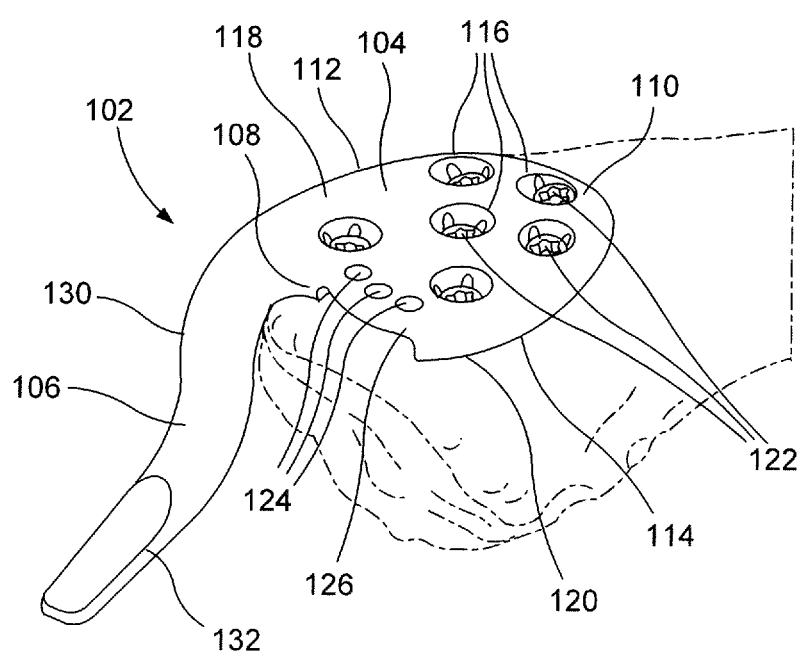
FIG. 2 shows a perspective view of a plate fixed on the superior aspect of the lateral clavicle using bone fixation elements according to the exemplary system of FIG. 1.

The present embodiments may be understood with reference to the following description and the appended drawings, wherein like elements are referred to with the same reference numerals. The present embodiments relate to the treatment of the acromioclavicular (AC) joint and, in particular, relates to the treatment of a dislocation of the AC joint using a hook plate. Exemplary embodiments describe an AC hook plate comprising a rounded shaft for placement along the lateral clavicle and a hook member extending therefrom. The rounded shaft permits an angulation of the plate so that the hook member may extend in a desired direction adapted to the patient's specific anatomy, while the shaft portion maintains contact with a superior aspect of the lateral clavicle. The hook member of an exemplary embodiment extends from the shaft of the hook plate directed so that, when the plate is positioned as desired, it extends at an angle relative to an axis perpendicular to an end of the clavicle inclined so that, when the plate is positioned as desired, it is angled relative to a longitudinal axis of the bone to increase an area of contact between the hook member and the acromion. It should be noted that any directional terms used herein are intended to refer to anatomical directional terms, as would be understood by those of skill in the art.

As shown in FIGS. 1-8, a system 100 for treating an AC joint dislocation according to an exemplary embodiment of the present disclosure comprises an AC hook plate 102 including a rounded shaft 104 configured to be positioned along a superior aspect of a lateral clavicle and a hook member 106 extending therefrom at an angle. The hook member 106 extends from the shaft 104 at an angle so that, when the hook plate 102 is positioned as desired, the hook member 106 may be hooked under an acromion. An angle of the hook member 106 relative to the shaft is selected to optimize contact between the hook member 106 and the acromion. In particular, the hook member 106 is angled relative to the shaft 104 so that, when the shaft 104 is seated on the superior aspect of the lateral clavicle in a desired position and orientation, the hook member 106 extends laterally away from the AC facet angled toward a lateral clavicle axis L, as those skilled in the art will understand, which extends through a middle of an AC facet to a conoid tubercle of the lateral clavicle. That is, the hook plate 102 is structured so that the hook member 106 extends at a desired angle relative to an axis A which, when the hook plate 102 is in the desired position and orientation, is parallel to the lateral clavicle axis L. In addition, a longitudinal portion 132 of the hook member 106, which is hooked under the acromion in an operative position, has a desired incline relative to an axis B that extends parallel to a plane P substantially matching a surface of the superior aspect on which the plate 102 is to be mounted. That is, the plate 102 is structured so that, when the hook plate 102 is in the desired position on the surface P of the superior aspect, the longitudinal portion 132 of the hook member 106 is angled relative to the axis B so that the hook member 106 extends under the acromion. The angulation of the longitudinal member 132 relative to the shaft 104 of the plate 102 is chosen to correspond to the angulation of an inferior surface of the acromion relative the superior surface of the lateral clavicle. In use, the longitudinal portion 132 of the hook member 106 is hooked under the acromion and the shaft 104 is pushed against the clavicle until the shaft is flush against the superior aspect of the lateral clavicle. If necessary, once the hook plate 102 is in this initial operative position, the rounded shaft 104 may be rotationally oriented along the superior aspect to direct the hook member 106 in an anterior and/or posterior direction to adapt the hook plate 102 to the patient's specific anatomy. In the desired position, the shaft 104 maintains contact with the superior aspect of the lateral clavicle as the hook plate 102 is rotated to obtain maximum contact surface between the hook member 106 and the acromion. As shown in FIG. 1, the system 100 may further comprise a reduction device 150 attachable to the hook plate 102 for reducing the clavicle and positioning the hook plate 102 relative to the AC joint, as described above.

Figure 3:
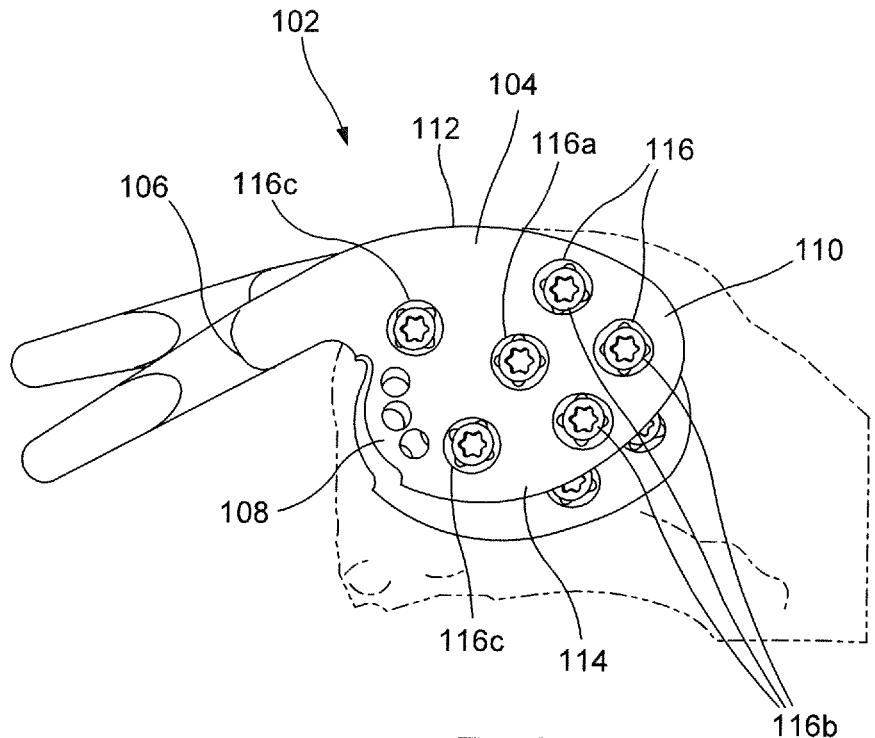
FIG. 3 shows a top plan view of the plate of FIG. 1, angulated in an anterior direction.
Figure 4:
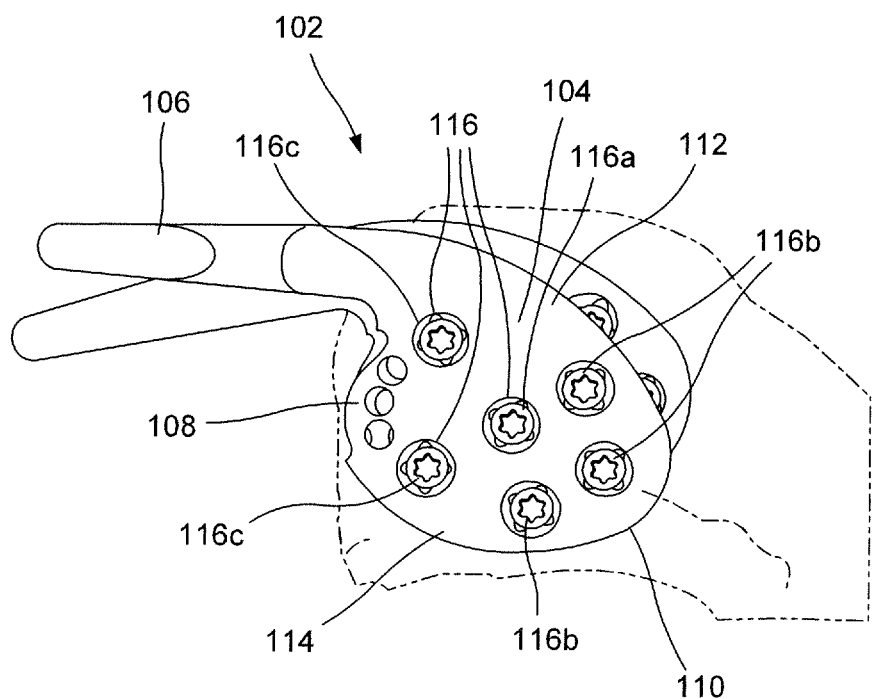
FIG. 4 shows a top plan view of the plate of FIG. 1, angulated in a posterior direction.

As described above, the shaft 104 of the hook plate 102 is configured so that the hook plate 102 may be rotationally oriented to direct the hook member 106 as required to conform to a patient's specific anatomy. As anatomy differs from patient to patient, (e.g., differing positions of acromion relative to the clavicle), rotating the hook plate 102 allows the hook member 106 to be directed more toward an anterior direction, as shown in FIG. 3, or to a posterior direction, as shown in FIG. 4, as required to properly position the hook member 106. The shaft 104 is configured to maintain contact with the superior aspect of the lateral clavicle while the hook plate 102 is rotated. In particular, a contour of the shaft 104 is rounded so that, rotational positioning of the hook plate 102 does not result in any portion of the shaft 104 protruding substantially beyond a surface of the lateral clavicle. The shaft 104 extends along a length from a first end 108 to a second end 110, with sides 112, 114 extending between the first and second ends 108, 110. The length of the shaft 104 (i.e., longest distance between the first and second ends 108, 110) is selected to be shorter than a length of an osteosynthesis plate that would customarily have been used for treating AC joint dislocations. For example, whereas a shaft of an osteosynthesis plate may have a length of 40 mm or more to extend across fractures of the clavicle, the shaft 104 may have a length of approximately 26 mm. This length of the shaft 104 is selected to be substantially equal to or less than a width of the surface of the superior aspect of the lateral clavicle to prevent protrusion of any portion of the shaft 104 upon angulation of the hook plate 102 regardless of its rotational orientation. In addition, the shorter length of the shaft 104 of the hook plate 102 is less invasive, requiring a smaller incision, reducing the risk of infection and producing a better cosmetic outcome. The shorter length of the shaft 104 also makes it easier to align the plate 102 along the clavicle and acromion and provides more space medial to the hook plate 102 for additional implants and/or grafts for reconstructing ligaments (e.g., CC) in chronic situations as would be understood by those skilled in the art.

The length of the shaft 104 may be slightly larger than a width of the shaft 104 (i.e., longest distance between the sides 112, 114). In one exemplary embodiment, in which the length of the shaft 104 is approximately 26 mm, the width of the shaft 104 may be approximately 23 mm. It will be understood by those of skill in the art, however, that these dimensions are exemplary only and that the shaft 104 may have any of a variety of dimensions so long as the shaft 104 has a substantially rounded shape and is sized relative to the portion of the particular clavicle on which it is to be mounted to prevent it from protruding beyond a surface of the lateral clavicle when mounted in the desired angular orientation in either an anterior or posterior direction. The first and second ends 108, 110 and the sides 112, 114 are all curved to form the substantially rounded shape of the shaft 104. Edges of the shaft 104 may also be curved, reducing plate prominence. To further reduce plate prominence, a thickness of the shaft 104 (i.e., a distance between a first surface 118 of the shaft 104 which, when the hook plate 102 is in an operative position faces away from the bone, and a second surface 120 of the shaft 104 which, when the hook plate 102 is in the operative position faces toward the bone) may be, for example, no more than 3.4 mm. This thickness, however, is exemplary only and may be varied, as desired.

The hook plate 102 may include a plurality of openings 116 extending through the shaft 104 from the first surface 118 to the second surface 120. The openings 116 are configured to receive bone fixation elements 122 therein for fixing the hook plate 102 to the bone. The openings 116 may extend through the shaft 104 in a variety of configurations. In one exemplary embodiment, a first one of the openings 116a extends through a substantially central portion of the shaft 104 while the remaining openings extend about the first opening 116a proximate a periphery of the shaft 104. For example, three of the openings 116b may extend along the periphery of the shaft 104 at the second end while two of the openings 116c extend through the shaft 104 along the first end 108.

Figure 5:
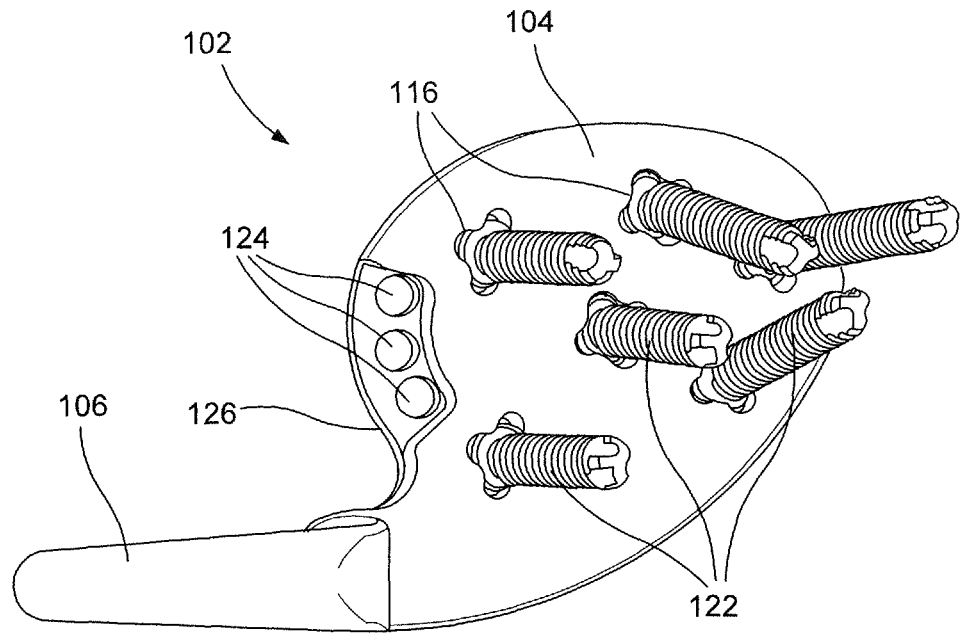
FIG. 5 shows a bottom plate view of the plate of FIG. 1 including bone fixation elements.

In one exemplary embodiment, as shown in FIG. 5, the openings 116 are configured as variable angle holes configured to receive bone fixation elements 122 therethrough along an angle relative to a central axis of the openings 116, within a permitted range of angulations. Thus, a surgeon or other use may insert bone fixation elements 122 (e.g., screws) therein along desired axes to fix the hook plate 102 to the bone. It may be desired to insert bone fixation elements 122 through the openings 102 so that axes of the bone fixation elements 122 converge at a point beyond the second surface 120 to improve anchorage of the hook plate 102 to the clavicle. Although the exemplary embodiment shows and describes all of the openings 116 as variable angle holes, it will be understood by those of skill in the art that all or some of the openings 116 may have different configurations for receiving bone fixation elements therethrough. For example, in another embodiment, one or more of the openings 116 may be locking holes extending through the shaft 104 along locking hole axes so that bone fixation elements 122 inserted therein engage the openings 116 and are locked therein along the locking hole axes. The openings 116 may be configured so that the locking hole axes converge beyond the second surface 120 of the shaft 104. In addition, although the exemplary embodiments show and describe the bone fixation elements 122 as screws, it will be understood by those of skill in the art that the bone fixation elements 122 may include other elements capable of insertion through the openings 116 to fix the hook plate 102 to the bone.

Figure 9:
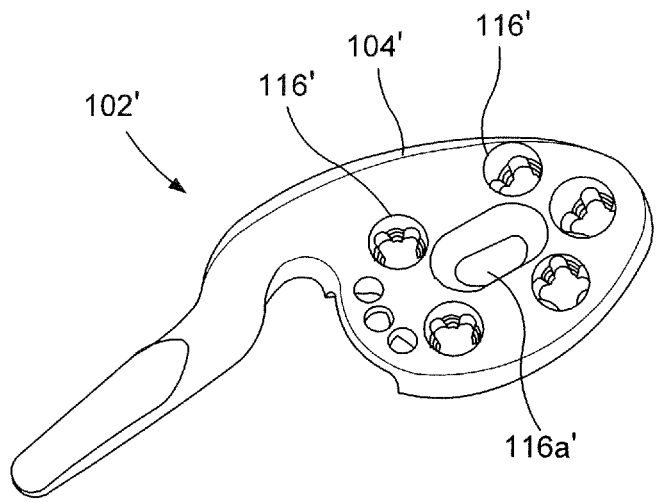
FIG. 9 shows a perspective view of a system according to an alternate embodiment of the present disclosure.

As noted above, one or more of the openings 116 may have a different configuration than the remaining openings 116. For example, as shown in FIG. 9, a first one 116a' of the openings 116' extending through a central portion of the shaft 104' may be configured as an elongated hole to facilitate preliminary fixation of the hook plate 102' to the clavicle via, for example, a wire, which may include a stop for compressing the plate to the bone, or a screw (e.g., non-locking/cortex), and allow adjustments to a position of the shaft 104' along the clavicle. Once the desired position of the hook plate 102' relative to the clavicle has been determined, fixation elements may be inserted through the remaining openings 116' (e.g., variable angle holes and/or locking holes) to fix the hook plate 102' to the bone.

Figure 6:
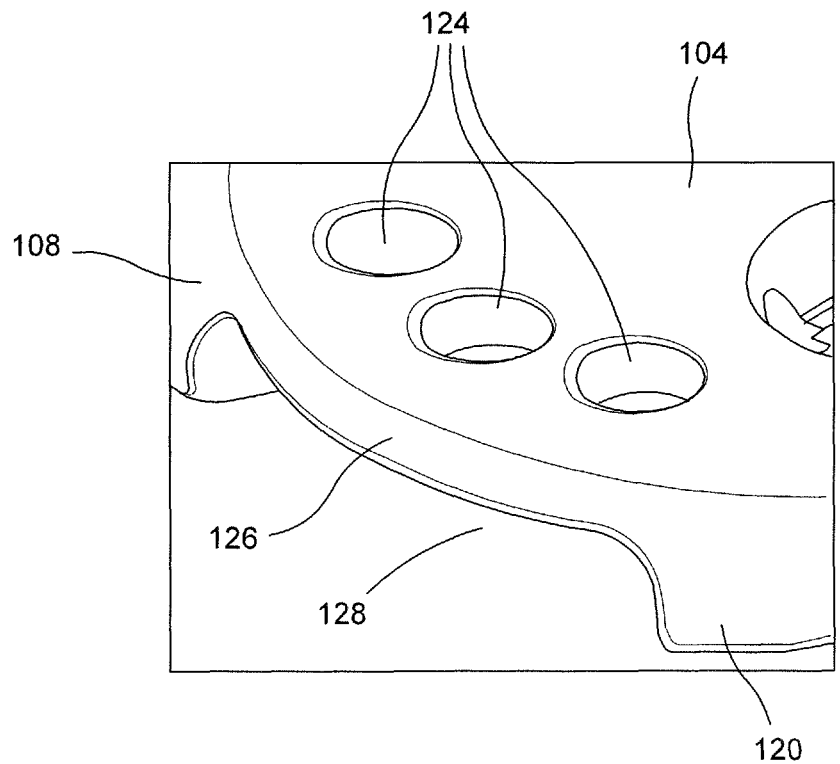
FIG. 6 shows an enlarged perspective view of a portion of the plate of FIG. 1.

As shown in FIG. 6, the hook plate 102 may also include suture holes 124 extending through the shaft 104 at the first end 108. The suture holes 124 are configured to receive sutures and/or needles for reattaching soft tissue such as, for example, the superior AC ligament and/or the deltopectoral fascia. The suture holes 124 may extend through an undercut portion 126 of the shaft 104, which includes a recess 128 extending into the second surface 120 so that the recess 128 is open at the first end 108. This undercut portion 126 permits a curved needle and/or suture to be easily passed through the suture holes 124, when the hook plate 102 is positioned against the bone.

As described above, the hook member 106 extends from the first end 108 of the shaft 104 along the first side 112 (e.g., a posterior side of the shaft 104). The hook member 106 includes a connecting portion 130 connecting a longitudinal portion 132 to the shaft 104 in an offset configuration. In other words, the longitudinal portion 132 is offset from a plane through which the shaft 104 extends so that, when the shaft 104 is positioned along the superior aspect of the lateral clavicle, the hook member 106—in particular, the longitudinal portion 132 of the hook member 106—may be hooked under the acromion. The connecting portion 130 extends from the first end 108 of the shaft 104 in an inferior direction and the longitudinal portion extends 132 from the connecting portion 130 in a lateral direction. Thus, when the hook plate 102 is in the operative position, the longitudinal portion 132 of the hook member 106 extends toward the acromion in the lateral direction.

As described above, an angulation/inclination of the hook member 106 may be described with respect to the anatomy of the lateral clavicle, when the hook plate 102 is placed in a desired position thereon. The lateral clavicle axis L is defined as an axis passing through a middle of the AC facet and the conoid tubercle of the lateral clavicle. As shown in FIG. 7, the hook member 106 extends from the shaft 104 at an angle relative to the axis A. When the shaft 104 is positioned along the substantially planar surface of the superior aspect of the lateral clavicle so that a length of the shaft 104 extends substantially along or parallel to the lateral clavicle L, the axis A also extends parallel to the lateral clavicle axis L. An axis C extends perpendicular to the lateral clavicle axis L and through the AC facet. In one embodiment, the hook member 106 may be angled between 15 and 30 degrees relative to the axis A and, in one particular embodiment, may be angled approximately 20 degrees relative to the axis A (i.e., approximately 110 degrees relative to the axis C). As described above and as will be described in further detail below, however, the shaft 104 may be rotationally oriented along the superior aspect—so that the length of the shaft 104 is angled with respect to the lateral clavicle axis L—to further adapt the hook plate 102 to the patient's specific anatomy. In particular, the shaft 104 may be rotationally oriented to move the hook member 106 in an anterior/posterior direction (FIGS. 3 and 4) to maximize contact between the hook member 106 and the acromion according to the patient's specific anatomy.

As shown in FIG. 8, the longitudinal portion 132 of the hook member 106 may also be inclined relative to the axis B, which extends parallel to the plane P extending along the superior aspect of the lateral clavicle along which the hook plate 102 is positioned. The plane P may be defined by three selected points along the substantially planar surface of the superior aspect. In the desired position, a bone-facing surface 134 of the shaft 104 is placed along the superior aspect so that, the axis B also extends substantially parallel to the bone-facing surface 134. An incline of the longitudinal portion 132 relative to the axis B is selected to optimize contact between the hook member 106 and the acromion. For example, the longitudinal portion may be inclined—toward an inferior direction—at an angle of between 10 and 20 degrees relative to axis B and, in one particular embodiment, may be inclined at an angle of approximately 15 degrees relative to the axis B. Since the acromion is generally offset and angled relative to the clavicle, the angulation and inclination of hook member 106 relative to the shaft 104 optimizes contact between the acromion and the hook member 106. Rotation of the hook plate 102 about the superior lateral aspect of the lateral clavicle in an anterior and/or posterior direction may further optimize contact of the hook member 102 with the acromion according to the patient's specific anatomy.

It will be understood by those of skill in the art that the angle and inclination of the hook member 106 described above is exemplary only and may be varied to optimize contact between the hook member 106 and the acromion. The angulation and inclination of the hook member 106 may correspond to a position of the acromion relative to an axis of the clavicle, when reduced. One study based on a 3D patient database has found the optimized angulation of the hook member 106 relative to axis C to be 111°±5.2° and the optimized inclination of the hook member 106 relative to the axis B to be 15°±4.7°. Thus, it will be understood by those of skill in the art that the angulation and inclination may be varied accordingly. It will also be understood by those of skill in the art, however, that these optimized values are exemplary only and that angulations/inclinations may extend beyond the noted range depending on a patient's specific anatomy.

The hook plate 102 may be manufactured in a variety of sizes and dimensions. In particular, hook plates 102 having different connecting portion 130 lengths may be available. For example, the connecting portion 130, which corresponds in length to a distance between the second surface 120 of the shaft 104 and the axis B, may be available in various sizes such as 10, 13 and 16 mm lengths. Thus, a surgeon may be able to select one of the hook plates 102 based on the patient's specific anatomy. The patient's anatomy may be determine via an x-ray, template or a trial implant to determine the appropriate size.

Figure 10:
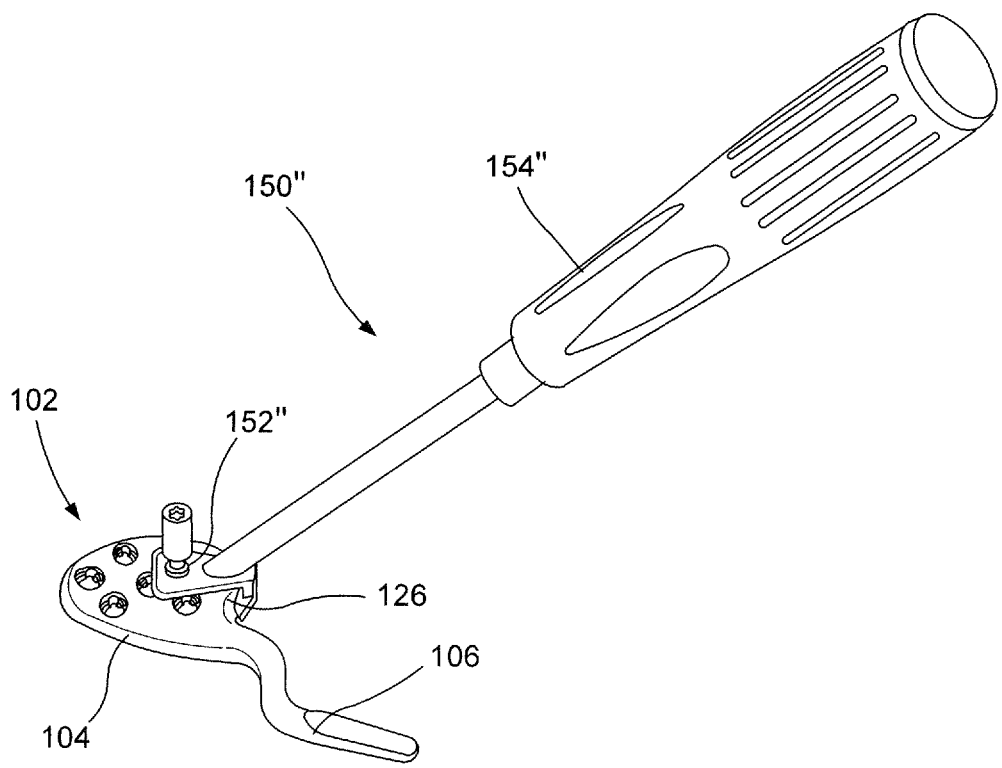
FIG. 10 shows a perspective view of a reduction device according to an alternate embodiment of the present disclosure.

The reduction device 150, as shown in FIG. 1, includes a base portion 152 releasably coupleable to the shaft 104 of the hook plate 102 and a handle member 154 extending from the base portion 152. The handle member 154 may extend from the base portion 152 at an angle so that, when the base portion 152 is coupled to the shaft 104, the surgeon or other user may reduce the clavicle of the AC dislocation and position the hook plate 102 using the handle member 154. The angle of the handle member 154 relative to the base portion 152 may be selected to optimize a reduction of the clavicle. In one embodiment, the base portion 152 may be sized and shaped to be coupled to the first surface 118 of the shaft 104 via, for example, a screw. In another embodiment, as shown in FIG. 10, a base portion 152" of a handle member 150' may be coupled to the shaft 104 via the undercut portion 126. It will be understood by those of skill in the art that the base portion 152 of the reduction device may be coupled to the hook plate 102 in any of a variety of ways, so long as the base portion 152 is coupled to the shaft 104 in a manner that permits insertion of the hook member 106 under the acromion and reduction of the clavicle via movement of the handle member 154. The reduction device 150 may further include an indicator such as a k-wire hole or laser etching to show a hook direction of the hook member 106 of the hook plate 106 to which it is connected, to facilitate insertion and correct alignment of the hook member 106 under the acromion.

According to an exemplary surgical method using the system 100, the reduction device is coupled to the shaft 104 of the hook plate 102 so that the hook plate 102 may be inserted into a patient's body and positioned, as desired, to treat an AC joint dislocation. In particular, the hook plate 102 is inserted through an incision in the skin and moved toward a target site of the AC joint using the handle member 154. The hook plate 102 is moved toward the target site until the hook member 106 is inserted under the acromion. Upon insertion of the hook member 106, the surgeon may move the shaft 104 of the hook plate 102 in the inferior direction to reduce the shaft 104 to the clavicle. Once the shaft 104 contacts the superior aspect of the lateral clavicle, a first (non-locking) bone fixation element may be inserted into one of the holes 116 of the plate 102 or the hole 116a' of the plate 102' to temporarily fix the plate 102, 102' to the clavicle. The hook plate 102 may then be angled by rotating the shaft 104 about a central point of the shaft 104 so that the hook member 106 is directed toward either the anterior or posterior direction to adapt to the patient's specific anatomy. In an optimum position, the shaft 104 should extend along the superior aspect while the hook member 106 achieves maximum contact with the acromion.

Once the hook plate 102 has been positioned as desired, bone fixation elements 122 are inserted through the openings 116 to fix the hook plate 102 to the clavicle. Fixation of the hook plate 102 to the clavicle maintains the clavicle and the acromion in a desired position relative to one another. The reduction device 150 may then be decoupled from the hook plate 102, leaving the hook plate 102 connected to the bone. If so desired, soft tissue such the superior AC ligament and/or the deltopectoral fascia may be attached to the hook plate 102 via the suture holes 124. Upon completion of the reduction, the incision may be sutured closed. Although the exemplary method describes and shows reduction and positioning of the hook plate 102 via the reduction device 150, it will be understood by those of skill in the art that the hook plate 102 may be similarly positioned to reduce and fix the lateral clavicle without the use of the reduction device 150.

As described above, the length of the shaft 104 of the hook plate 102 permits the use of additional implants such as, for example, clavicle shaft plates positioned medially of the hook plate 102. According to another exemplary embodiment, however, hook plates may be configured for the treatment of both AC joint dislocations along with fractures and associated soft tissue injuries of the lateral clavicle such as, for example, Neer type II, Jaeger and Breitner type II. These hook plates may have shafts configured to be positioned along the shaft of the lateral clavicle and may be manufactured in a variety of lengths. For example, hook plates may be manufactured in a short length, as shown in FIG. 11, and a long length, as shown in FIG. 12.

Figure 11:
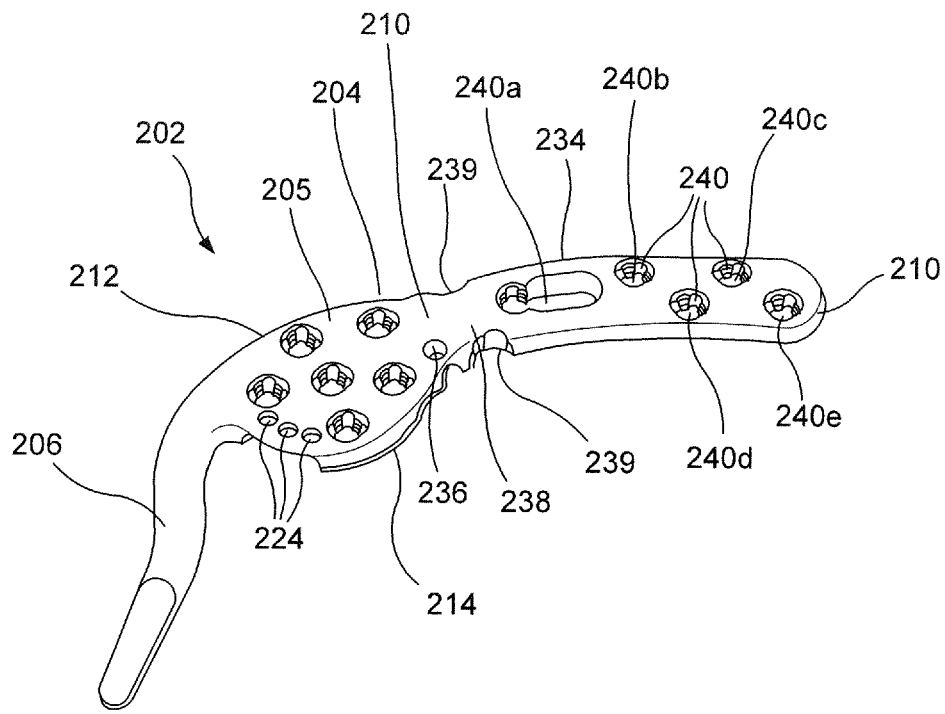
FIG. 11 shows a perspective view of a plate according to another exemplary embodiment of the present disclosure.
Figure 12:
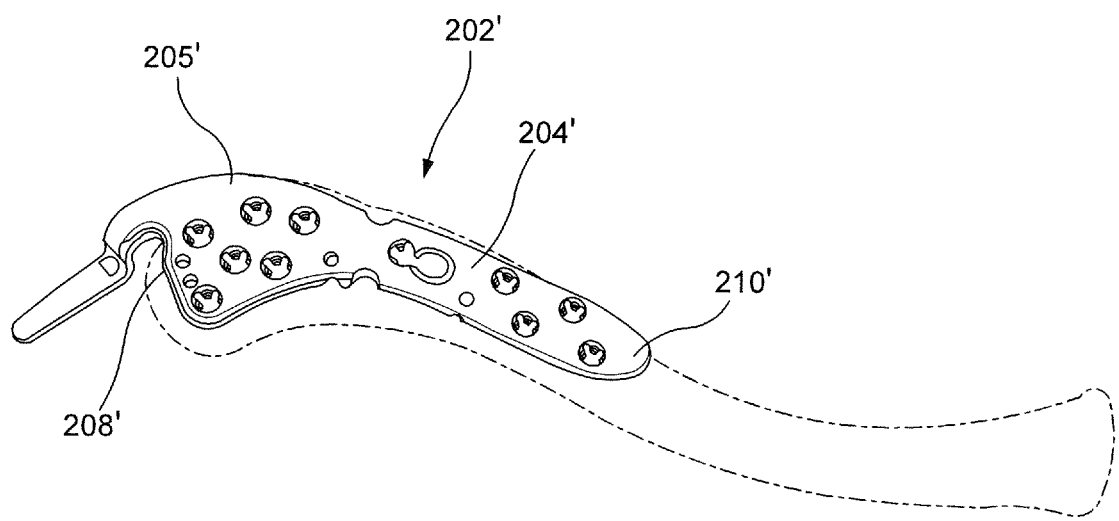
FIG. 12 shows a perspective view of a plate according to an alternate embodiment of the present disclosure.

As shown in FIG. 11, a hook plate 202 according to another exemplary embodiment may be configured for the treatment of an AC joint. Similarly to the hook plate 102, the hook plate 202 comprises a shaft 204 and a hook member 206. The hook member 206 may be substantially similar to the hook member 106, the hook member 206 being angulated and/or inclined to optimize contact with the acromion, in an operative position. The shaft 204, however, includes a lateral portion 205 substantially similar to the shaft 104 and a medial portion 234 extending medially from the lateral portion 205 to be positioned along the shaft of the clavicle for the treatment of fractures and/or soft tissue injuries. A length of the shaft 204 of the hook plate 202 may be shaped (e.g., curved) to correspond to a shape of the clavicle. For example, the shape of the shaft 204 may be determined using a polynomial equation derived from a mean shape bone model or a patient specific scan of the bone.

In particular, similarly to the shaft 104, the lateral portion 205 is sized to be positioned on a superior aspect of the lateral clavicle and may have a substantially rounded shape so that the hook member 206 may be angulated in an anterior and/or superior direction to accommodate a patient's specific anatomy (i.e., position of the acromion relative to the clavicle). The lateral portion 205 may include all of the features of the shaft 104 including, but not limited to, openings 216 extending through the lateral portion 205 for receiving bone fixation elements and suture holes 224 for receiving sutures/needles for attaching soft tissues. The lateral portion 205 may additionally include one or more additional suture holes 236 proximate a second end 210 of the lateral portion 205, along an anterior side 214 and/or a posterior side 212 of the lateral portion 205 and/or along the shaft portion 204, 234 for reattachment to the deltoid, the pectoralis major and/or any other muscle, tendon and/or ligament attached to the lateral end of the clavicle and/or any bone fragment that may or may not be attached to these muscles, tendons or ligaments. Although the lateral portion 205 is shown and described as having a rounded shape, it will be understood by those of skill in the art that the lateral portion 205 may have other shapes so long as the lateral portion 205 is sized and shaped to be positioned along the superior aspect of the lateral clavicle. For example, as shown in FIG. 12, a lateral portion 205' of a shaft 204' of a plate 202' may be taper from a first end 208' toward a second end 210' of the shaft 204'.

The medial portion 234 may extend medially from the lateral portion 205 and may be connected to the lateral portion 205 via a reduced width portion 238 of the hook plate 202. The reduced width portion 238 defined by recesses 239 extending into posterior and/or anterior sides 212, 214 of the hook plate 202. The reduced width portion 238 facilitates bending adjustments of the lateral portion 205 relative to the medial portion 234. The medial portion 234 may include a plurality of openings 239. The openings 239 may have any of a variety of configurations including, for example, variable angle holes, locking holes, combination variable angle and compression holes, etc. In one exemplary embodiment, a first one of the openings 240a proximate the reduced width portion 238 may be configured as a combination variable angle and compression hole. A compression portion of the first opening 240a may be used for out-of-plane bending. Remaining openings 240b-240e may be configured as variable angle holes and/or locking holes. Openings 240b, 240c and 240d, 240e may be positioned on opposite sides of a central axis of the shaft 204 and may be offset from one another along a length of the shaft 204. It will be understood by those of skill in the art, however, that this configuration of openings 240 is exemplary only and that the medial portion 234 may include any number of openings 210 having any of a variety of configurations to permit fixation of the shaft 204 to the clavicle and/or reduction of fractures of the clavicle. A medial end 210 of the plate shaft 204 may include a portion where the plate 202 thickness and/or width is progressively reduced towards the end of the plate 202. This serves to reduce the prominence of the end 210 of the plate 202 and therefore the potential of inducing pain and discomfort to the patient.

Figure 13:
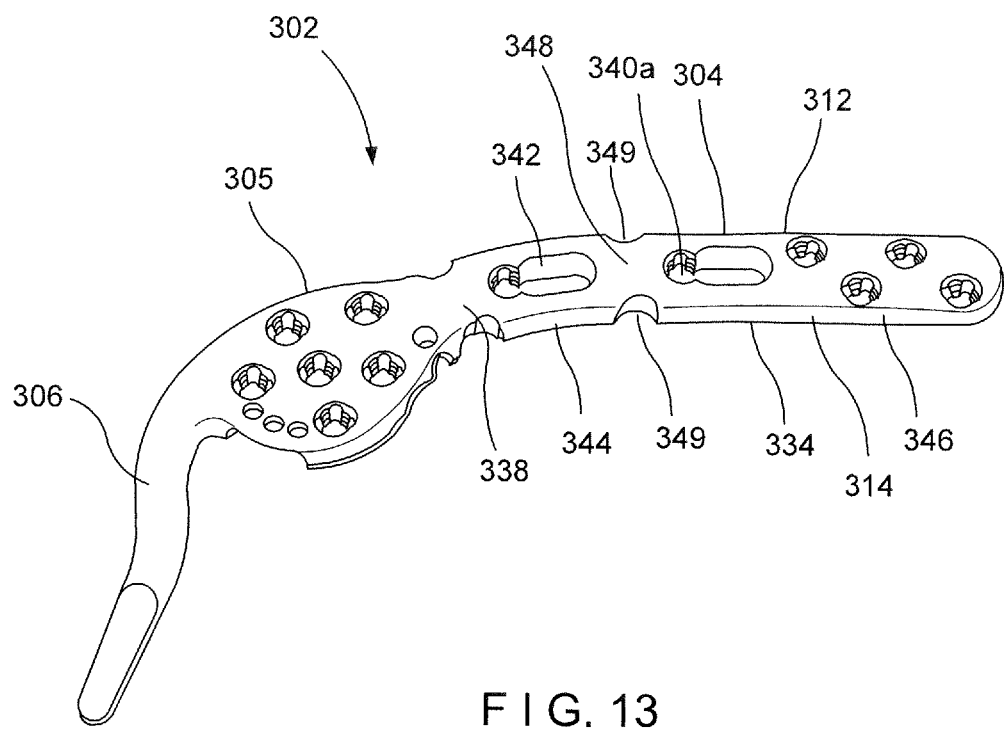
FIG. 13 shows a perspective view of a plate according to yet another exemplary embodiment of the present disclosure.
Figure 14:
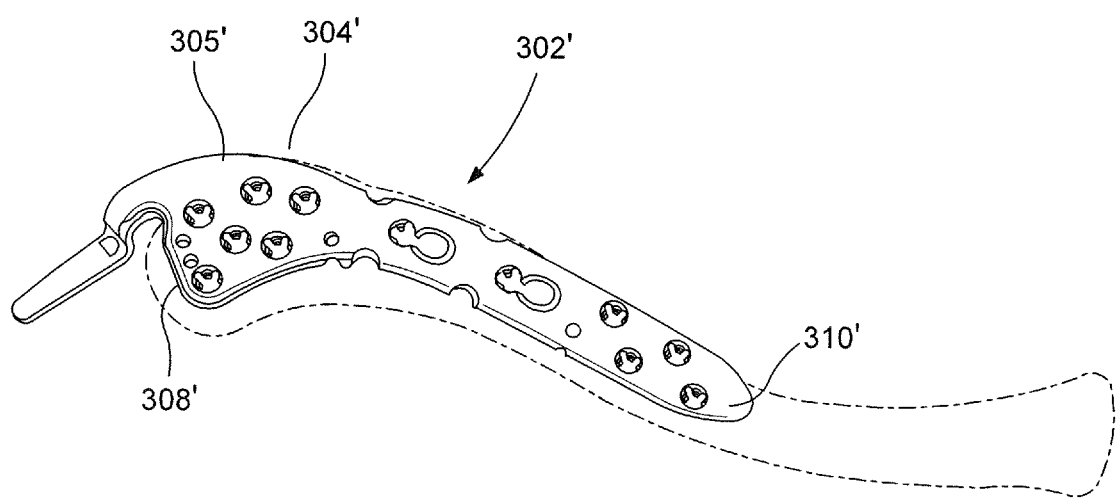
FIG. 14 shows a perspective view of a plate according to another alternate embodiment of the present disclosure.

In another embodiment, as shown in FIG. 13, a hook plate 302 may be substantially similar to the hook plate 202, having all of the same features of the hook plate 202, but with a longer length. Similarly to the hook plate 202, the hook plate 302 includes a hook member 306 connected to the shaft 304, the shaft 304 including a lateral portion 305 and a medial portion 334 connected to one another via a first reduced width portion 338. The lateral portion 305 may be substantially similar to the shaft 104 of the plate 102 or the lateral portion 205 of the plate 202. Similarly to the plate 202, the lateral portion 305 may be rounded, as shown in FIG. 13. The lateral portion 305, however, may have any of a variety of shapes so long as the lateral portion 305 is configured to be positioned along a superior aspect of the lateral clavicle. For example, as shown in FIG. 14, a lateral portion 305' of shaft 304' of a plate 302' may taper from a first end 308' of the shaft 304' toward a second end 310' of the shaft 304'.

The medial portion 334, however, is longer than the medial portion 234. The medial portion 334 may include an additional opening 342 positioned laterally of an opening 340a. In one exemplary embodiment, this additional opening 342 may be configured as combination variable angle and compression hole. It will be understood by those of skill in the art, however, that the opening 342 may have any of a variety of configurations for receiving a bone fixation element. A first portion 344 of the medial portion 334 including the additional opening 342 may be connected to a second portion 346 of the medial portion 334 including remaining openings 340 via a second reduced width portion 348. This second reduced width portion 348 may be substantially similar to the first reduced width portion. The second reduced width portion 348 is defined via recesses 349 extending into posterior and anterior sides 312, 314 of the shaft 304 to permit a bending adjustment between the first and second portions 344, 346 of the medial portion 334 of the shaft 304 to better suit the patient's specific anatomy. In a further embodiment, one or more additional reduced-width portions may be added along the shaft 304 medially of the second reduced-width portion 348. The shaft 304 may be bent along these reduced-width portions according to the patient's anatomy.

The hook plates 202 and 302 may be used in a manner substantially similar to the hook plate 102 of system 100. In particular, the hook plates 202, 302 may be implanted in the body using a reduction device substantially similar to the reduction device 150 of the system 100. The hook members 206, 306 may be hooked under the acromion and the shafts 204, 304 pushed against the shaft of the clavicle to reduce the clavicle. It will be understood by those of skill in the art that the hook plates 202, 302 may be adjusted to suit the patient's specific anatomy (i.e., a shape of the patient's clavicle) through angulation, for example, by bending the plate at the reduced width portions 238, 338, 348. The lateral portions 205, 305 are positioned along the superior aspect of the lateral clavicle and fixed thereto via bone fixation elements, as described above with respect to the plate 102. The medial portions 234, 334 are positioned along the shaft of the clavicle and fixed thereto via any number of bone fixation elements inserted through openings 240, 340, 342.

It will be understood by those of skill in the art that modifications and variations may be made in the structure and methodology of the present embodiment, without departing from the spirit or the scope of the embodiments. Thus, it is intended that the present embodiments cover the modifications and variations of these embodiments provided that the come within the scope of the appended claims and their equivalents.

What is claimed is:

1. A bone plate for treating acromioclavicular dislocations, comprising:
   a shaft including a lateral portion sized and shaped to be positioned along a superior aspect of a lateral clavicle, the shaft including a plurality of openings extending therethrough for receiving bone fixation elements therein; and
   a hook member extending from the shaft so that, in an operative position, the hook member is hooked under an acromion and the lateral portion of the shaft is positioned on the superior aspect of the lateral clavicle, the lateral portion of the shaft being substantially rounded so that the hook member is movable in one of an anterior direction and a posterior direction while the shaft maintains contact with the superior aspect of the lateral clavicle without any portion of the lateral portion of the shaft protruding beyond a surface of the lateral clavicle.

2. The bone plate of claim 1, wherein the hook member extends from the shaft at an angle relative to a longitudinal axis of the shaft.

3. The bone plate of claim 2, wherein the angle of the hook member relative to the longitudinal axis of the shaft ranges from between 15 and 30 degrees.

4. The bone plate of claim 3, wherein the angle of the hook member relative to the longitudinal axis of the shaft is 21 degrees.

5. The bone plate of claim 1, wherein the hook member includes a connecting portion and a longitudinal portion, the longitudinal portion being inclined in an inferior direction relative to a longitudinal axis of the clavicle on which the bone plate is to be mounted.

6. The bone plate of claim 5, wherein an inclination of the longitudinal portion relative to a bone-facing surface of the shaft ranges from between 10 and 20 degrees.

7. The bone plate of claim 6, wherein the inclination of the longitudinal portion relative to the bone-facing surface is 15 degrees.

8. The bone plate of claim 1, wherein the shaft is defined by first and second ends along with anterior and posterior sides extending therebetween, the hook member extending from the first end along the posterior side.

9. The bone plate of claim 1, wherein a maximum length of the lateral portion of the shaft is selected to be no larger than a width of the surface of the superior aspect of the clavicle.

10. The bone plate of claim 1, wherein each of the openings is configured as one of a variable angle hole and a locking hole.

11. The bone plate of claim 1, further comprising an elongated opening extending through a central portion of the lateral portion of the shaft.

12. The bone plate of claim 1, further comprising a plurality of suture holes extending through the lateral portion of the shaft for attaching soft tissue thereto.

13. The bone plate of claim 12, wherein the suture holes extend through an undercut portion of the shaft.

14. The bone plate of claim 1, wherein the shaft includes a medial portion extending from the lateral portion in a medial direction so that, in the operative position, the medial portion extends along a shaft portion of the clavicle, the medial portion including a plurality of openings extending therethrough for receiving bone fixation elements therein.

15. The bone plate of claim 14, wherein the medial portion is connected to the lateral portion via a reduced width portion permitting bending adjustment of the bone plate between the lateral and medial portions.

\* \* \* \* \*